(12) United States Patent
Heneveld

(10) Patent No.: US 11,324,581 B2
(45) Date of Patent: May 10, 2022

(54) SILICONE PROSTHESIS DELIVERY APPARATUS AND METHODS OF USE

(71) Applicant: Conical Cover LLC, Boca Raton, FL (US)

(72) Inventor: Scott Hyler Heneveld, Whitmore, CA (US)

(73) Assignee: Conical Cover LLC, Boca Raton, FL (US)

( * ) Notice: Subject to any disclaimer, the term of this patent is extended or adjusted under 35 U.S.C. 154(b) by 12 days.

(21) Appl. No.: 16/999,536

(22) Filed: Aug. 21, 2020

(65) Prior Publication Data
US 2021/0052359 A1 Feb. 25, 2021

Related U.S. Application Data

(60) Provisional application No. 62/891,342, filed on Aug. 24, 2019.

(51) Int. Cl.
*A61F 2/12* (2006.01)
*A61F 2/00* (2006.01)

(52) U.S. Cl.
CPC .............. *A61F 2/0095* (2013.01); *A61F 2/12* (2013.01)

(58) Field of Classification Search
CPC .. A61F 2/0095; A61F 2/12; A61F 2230/0067; A61F 2250/0021; A61F 2250/0039; A61F 2250/0018
See application file for complete search history.

(56) References Cited

U.S. PATENT DOCUMENTS

| 3,138,821 | A | 6/1964 | Macciocchi et al. |
| 5,052,554 | A | 10/1991 | Leonard |
| 6,383,191 | B1 | 5/2002 | Zdeblick et al. |
| 8,211,173 | B2 | 7/2012 | Keller et al. |
| 8,550,090 | B2 | 10/2013 | Keller et al. |
| 8,555,893 | B2 | 10/2013 | Keller et al. |
| 9,402,713 | B2 | 8/2016 | Keller et al. |
| 10,136,988 | B2 | 11/2018 | Keller et al. |
| 10,213,294 | B2 | 2/2019 | Keller et al. |
| 2007/0276485 | A1 | 11/2007 | Abell et al. |

(Continued)

*Primary Examiner* — Brian A Dukert
*Assistant Examiner* — Rebecca Lynee Zimmerman
(74) *Attorney, Agent, or Firm* — Master Key IP, LLP; Justin G. Sanders

(57) ABSTRACT

A silicone prosthesis delivery apparatus and associated methods are disclosed for facilitating the transport and subsequent insertion of a silicone prosthesis into a surgically developed pocket of a patient. In at least one embodiment, a flexible, substantially funnel-shaped delivery sleeve is configured for receiving and subsequently expelling the prosthesis therefrom. The delivery sleeve provides a substantially conical-shaped entry portion and a substantially conical-shaped exit portion, the entry portion and exit portion opposingly positioned and joined with one another so as to form a relatively larger diameter middle section. A tapered free end of the entry portion provides an entry opening configured for allowing the prosthesis to selectively pass therethrough when the prosthesis is inserted into the delivery sleeve. A tapered free end of the exit portion provides an exit opening configured for allowing the prosthesis to selectively pass therethrough when the prosthesis is expelled from the delivery sleeve.

15 Claims, 6 Drawing Sheets

(56) References Cited

U.S. PATENT DOCUMENTS

| | | | |
|---|---|---|---|
| 2014/0187666 A1* | 7/2014 | Aizenberg | A61L 15/46 523/113 |
| 2015/0032208 A1* | 1/2015 | Preissman | A61F 2/12 623/8 |
| 2016/0095697 A1* | 4/2016 | Anderson | A61F 2/12 623/8 |
| 2016/0199174 A1 | 7/2016 | Keller et al. | |
| 2017/0181841 A1* | 6/2017 | Weinzweig | A61B 90/08 |
| 2020/0008923 A1* | 1/2020 | Geiger | A61B 17/3431 |

* cited by examiner

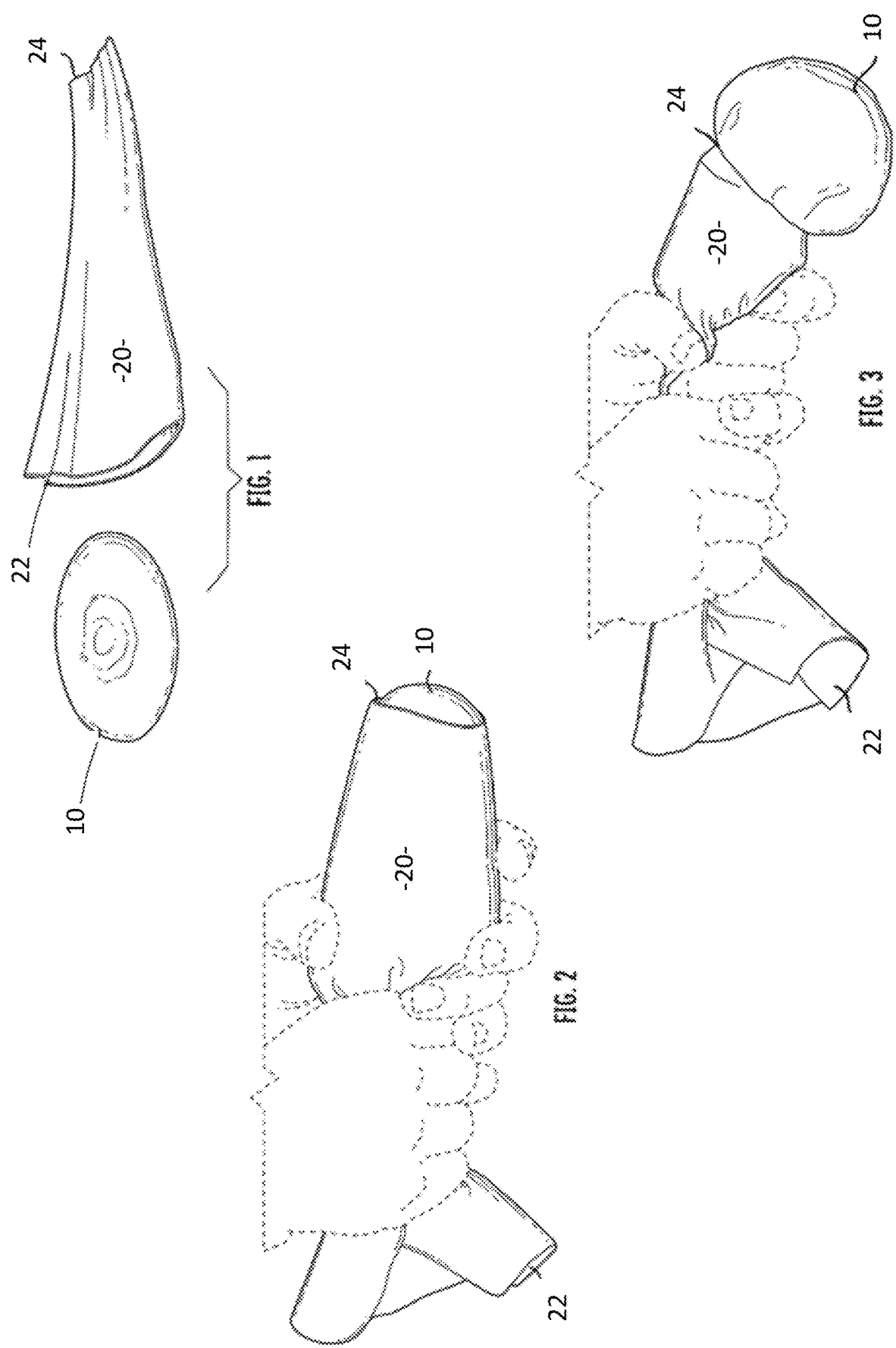

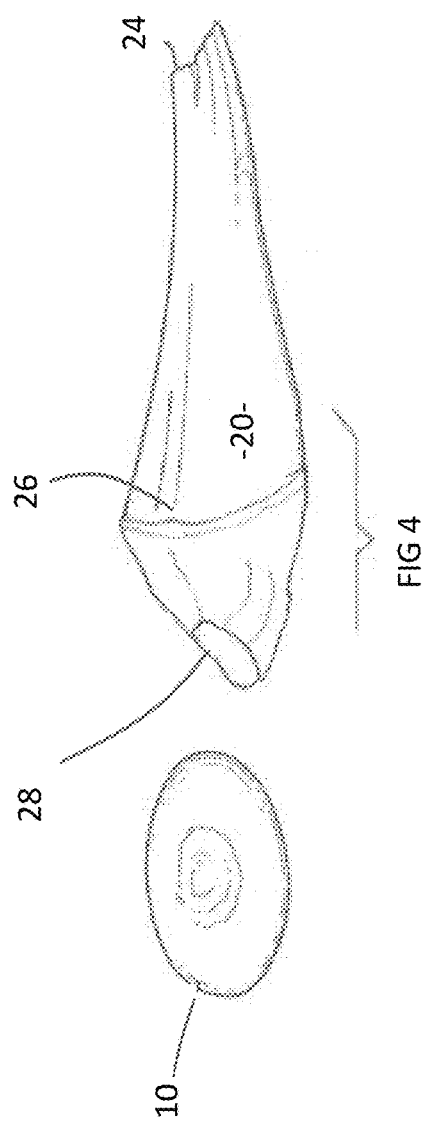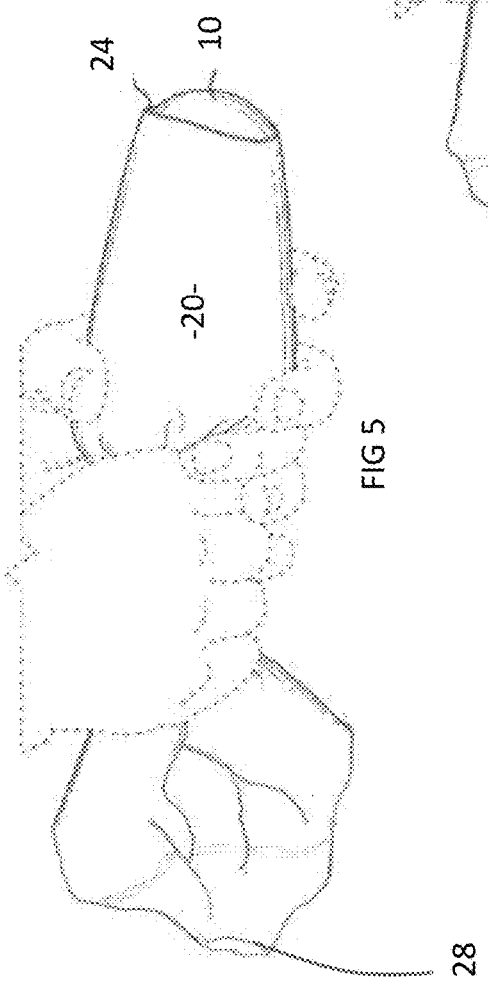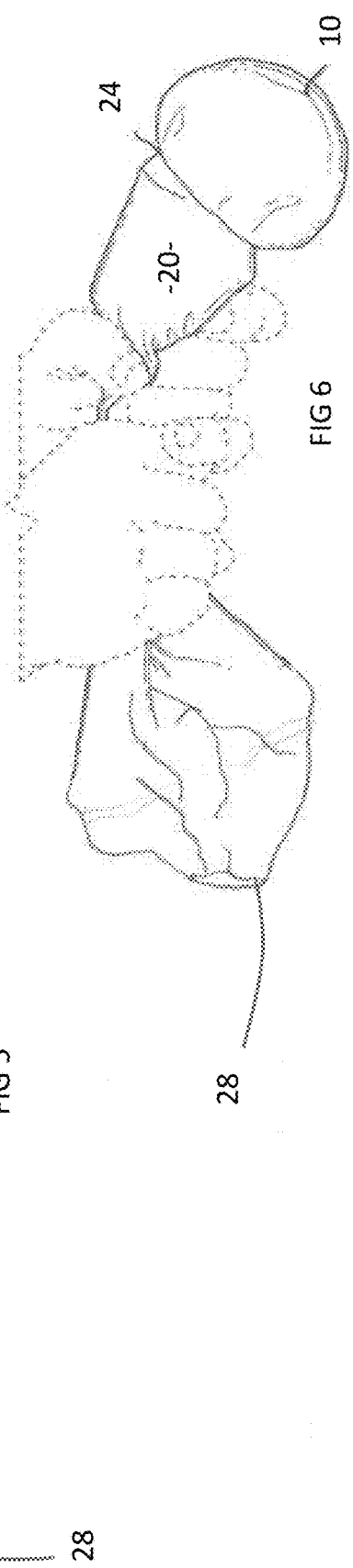

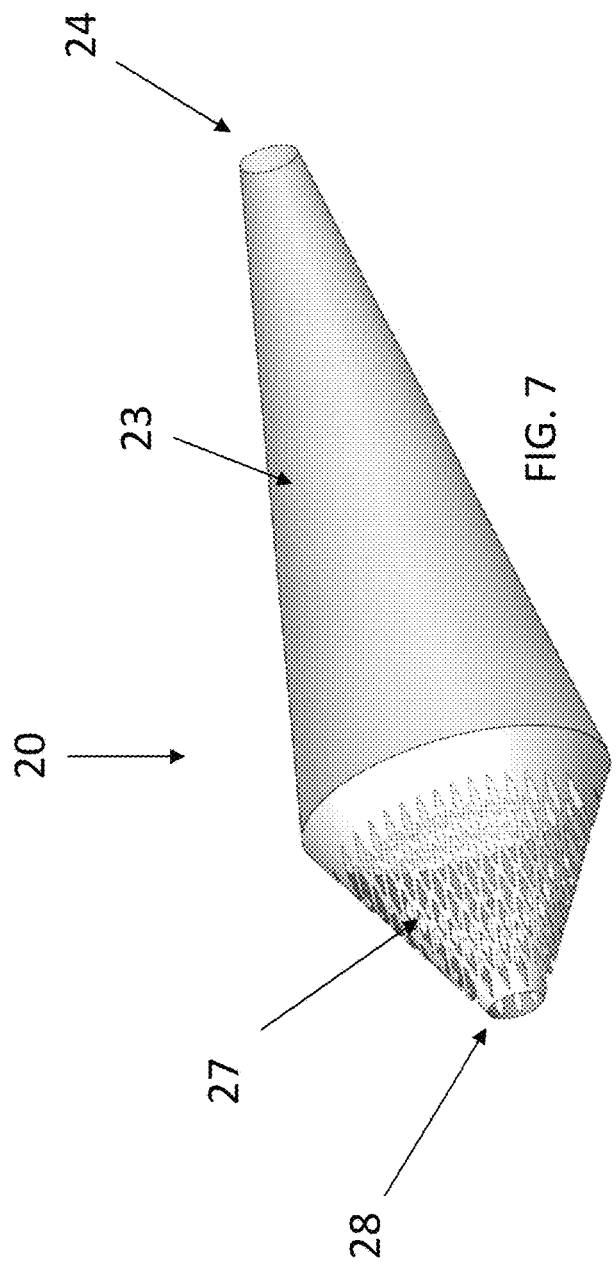
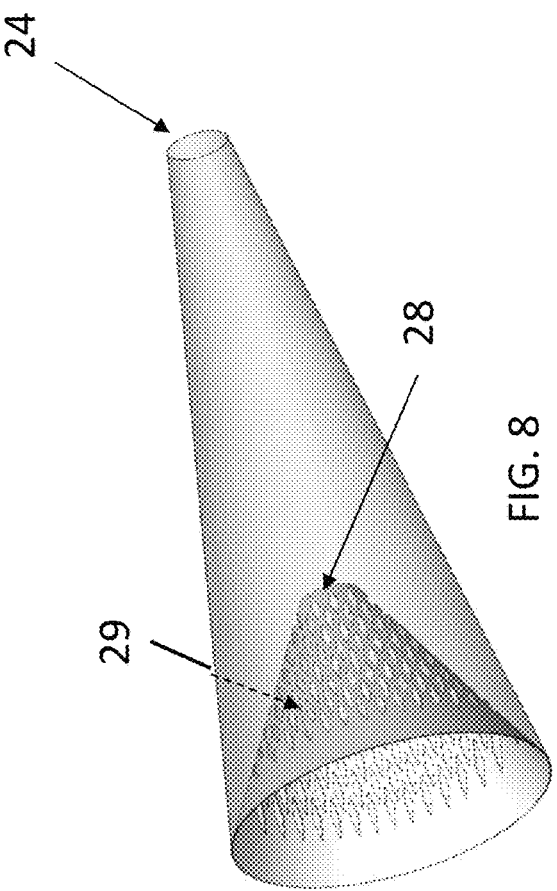

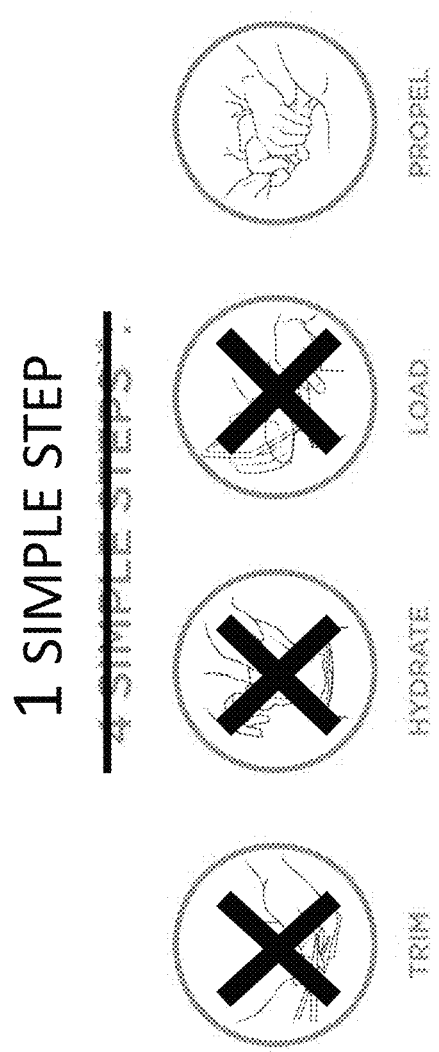

SILICONE PROSTHESIS DELIVERY APPARATUS AND METHODS OF USE

RELATED APPLICATIONS

This application claims priority and is entitled to the filing date of U.S. provisional application Ser. No. 62/891,342, filed on Aug. 24, 2019. The contents of the aforementioned application are incorporated herein by reference.

BACKGROUND

The subject of this patent application relates generally to prosthesis delivery devices, and more particularly to a silicone prosthesis delivery apparatus and associated methods of use for facilitating the transport and subsequent insertion of a silicone implant, such as a breast prosthesis, into a surgically developed pocket of a patient.

Applicant hereby incorporates herein by reference any and all patents and published patent applications cited or referred to in this application.

By way of background, silicone implants have been in worldwide use for many years. While marketing of such implants was halted within the United States for a period of time, the use of silicone implants has resumed within the United States. Traditional surgical approaches of inserting prefilled silicone implants require the use of larger incisions in comparison to saline implants which can be inserted through small incisions which are later filled in situ with saline. The larger incisions are not preferable to many patients.

An additional concern with the use of silicone implants is that the longevity and integrity of the implants can be damaged by the conventional insertion process. A typical insertion process involves direct finger handling and prodding by the surgeon of the implant in order to insert it into the surgical pocket. Implant failures can be associated with an area of high stress to the outer surface of the implant. The stressed areas are believed to correlate to excessive pressure applied by finger handling and prodding of the implant and/or damage associated with damage of the implant surface by a "touching" injury that damages the implant.

Another concern is contamination of the implant upon placement in the breast pocket. Capsular contracture is the leading complication after breast augmentation. The contracture is believed to be the result of a low-grade bacterial infection or the formation of a biofilm around implants that causes severe inflammation. Although bacterial contamination has been implicated in capsule formation, the process of contracture is thought to be multifactorial, including inflammatory responses of the immune system. There are several factors that contribute to capsular contracture: 1) implant texture, 2) implant type, 3) incision type, 4) rupture/leakage, and 5) pocket contamination with blood, bacteria, and synthetic fibers. Refining the surgical technique to minimize the implant's contact with the surgeon's gloves and patient's skin are believed to reduce the incidence of capsular contracture. The development of the Keller Funnel, a mechanical insertion device, allowed for a no-touch implant technique by giving an alternative to hand-placement of implants into breast pockets. The Keller Funnel is constructed of vinyl film with a lubricous hydrophilic coating. The exit opening of the Keller Funnel is cut to the implant size and then hydrated before the implant is poured directly from the packaging into the funnel. The funnel is placed about 1 centimeter inside the dissected pocket, and the implant is expelled through the funnel and into the pocket as a no-skin touch technique. The funnel makes implant insertion safer by decreasing the stress to the implant shell, minimizing contact with the patient's skin and the contact with the surgeon's gloves during insertion. The funnel also affords time savings by reducing surgical duration for implant insertion.

However, due to the expensive lubricious hydrophilic coating utilized by the Keller Funnel, much of the cost savings attributed to reduced surgical time and improved outcomes are negated. Although the clinical benefits are documented and appreciated by plastic surgeons, the high cost of the device prevents many surgeons from adopting the device in their practice. In addition, the high cost prohibits the use of a separate funnel for each the left and right breasts. The same funnel is used for both sides, thus inducing the risk of cross-contamination on the second implantation. Multiple uses of the device can result is sloughing of the surface hydrophilic coating, thus exposing the high friction vinyl substrate to the silicone implant shell. This could result in elevated stress on the implant shell during implantation, with possible damage or susceptibility to bacterial infection or biofilm formation. The Keller Funnel also has a large opening to allow entry of the silicone implant. This large opening provides a means for the silicone implant to unintentionally slide from the funnel and off the sterile field, thus requiring vigilance by the clinician to maintain the implant inside the funnel.

Thus, there remains a need for a cost-effective funnel for delivering breast implants that will allow more patients to clinically benefit from a no-skin touch technique, while also reducing the attention needed by the clinician to prevent the implant from unintentionally escaping from the funnel. Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing a silicone prosthesis delivery apparatus and associated methods for facilitating the transport and subsequent insertion of a silicone prosthesis into a surgically developed pocket of a patient. In at least one embodiment, a flexible, substantially funnel-shaped delivery sleeve is configured for receiving and subsequently expelling the prosthesis therefrom. The delivery sleeve provides a substantially conical-shaped entry portion and a substantially conical-shaped exit portion, the entry portion and exit portion opposingly positioned and joined with one another so as to form a relatively larger diameter middle section. A tapered free end of the entry portion provides an entry opening configured for allowing the prosthesis to selectively pass therethrough when the prosthesis is inserted into the delivery sleeve. A tapered free end of the exit portion provides an exit opening configured for allowing the prosthesis to selectively pass therethrough when the prosthesis is expelled from the delivery sleeve. Thus, with the prosthesis positioned within the delivery sleeve, the delivery sleeve is capable of being manipulated to conform to the shape of the prosthesis as well as to apply pressure to direct the prosthesis along a length of the delivery sleeve and toward the exit opening, such that the prosthesis may be expelled from the delivery sleeve through the exit opening.

An exemplary method for preparing the silicone prosthesis delivery apparatus includes the steps of inserting a prosthesis through the entry opening of the entry portion of the delivery sleeve, such that the prosthesis is positioned within the delivery sleeve; folding each of the opposing ends of the delivery sleeve so as to obstruct each of the entry opening and exit opening, thereby preventing the prosthesis from unintentionally exiting the delivery sleeve; and positioning the delivery sleeve within a sterile barrier packaging.

It is one aspect of at least one embodiment to provide an apparatus and a process for facilitating the distribution, transport and subsequent delivery of a silicone implant into a surgically developed pocket of a patient.

It is a further aspect of at least one embodiment to provide an apparatus and process that allows insertion of a silicone implant through a sleeve defining a small diameter outlet into a patient without direct hand manipulation of the implant. In at least one such embodiment, the sleeve is constructed of a material with a lubricious additive or additives added during the processing of the film.

It is a further aspect of at least one embodiment to provide an apparatus and process that allows insertion of a silicone implant through a sleeve defining a small diameter outlet into a patient without direct hand manipulation of the implant. In at least one such embodiment, the sleeve is constructed of a material with a lubricious additive or additives added during the processing of the film which can be used in combination with a surgical lubricant or lubricants, which may be applied to the sleeve either at the factory or in the clinic during the insertion process.

It is yet a further and more particular aspect of at least one embodiment to provide a process and apparatus that allows for the retention of a silicone implant in a sleeve with small diameter inlet and small diameter exit and for a "touchless" insertion of a silicone implant into a surgical pocket. In at least one such embodiment, the construct at the inlet region is elastic to allow reduced entry pressure for placement of the implant and subsequent retention of the implant within the apparatus.

It is yet a further and more particular aspect of at least one embodiment to provide a process and apparatus that allows for the silicone implant to be "pre-loaded" at the factory into the sleeve and then placed together as an assembly in a sterile barrier package for sterilization and then delivered to the hospital setting to provide the facilitation of a truly "touchless" insertion of a silicone implant into a surgical pocket.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1 is a perspective view of an exemplary silicone prosthesis delivery apparatus along with an exemplary silicone prosthesis, in accordance with at least one embodiment;

FIGS. 2 and 3 are further perspective views thereof, illustrating the prosthesis positioned within a delivery sleeve of the apparatus, along with hand manipulation of the prosthesis via the delivery sleeve, in accordance with at least one embodiment;

FIG. 4 is a perspective view of a further exemplary silicone prosthesis delivery apparatus along with an exemplary silicone prosthesis, in accordance with at least one embodiment;

FIGS. 5 and 6 are further perspective views thereof, illustrating the prosthesis positioned within an delivery sleeve of the apparatus, along with hand manipulation of the prosthesis via the delivery sleeve, in accordance with at least one embodiment;

FIGS. 7 and 8 are perspective views of a further exemplary silicone prosthesis delivery apparatus, in accordance with at least one embodiment;

FIG. 11 is a diagram illustrating an exemplary method of utilizing the exemplary silicone prosthesis delivery apparatus to insert a silicone implant into a surgically developed pocket of a patient, in accordance with at least one embodiment.

Figure 9:
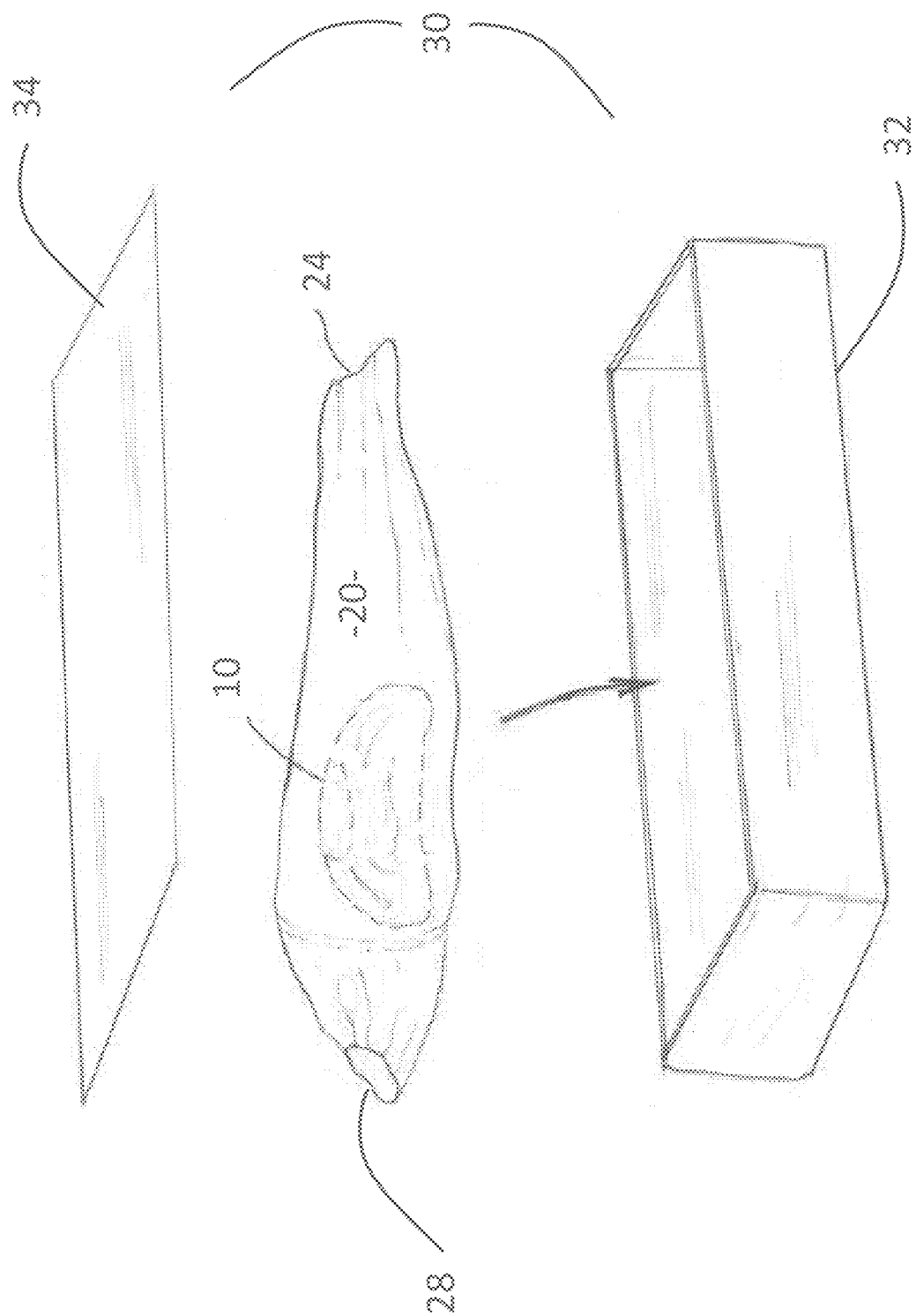
FIG. 9 is a further perspective view thereof, illustrating the prosthesis positioned within an delivery sleeve of the apparatus, along with the apparatus being positionable within a transport container, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Turning now to FIGS. 1-3, there are shown perspective views of an exemplary embodiment of a silicone prosthesis delivery apparatus configured for facilitating the transport and subsequent insertion of a silicone prosthesis 10 into a surgically developed pocket of a patient. In at least one embodiment, the apparatus comprises a flexible, substantially funnel-shaped delivery sleeve 20 able to receive and expel the prosthesis 10, as illustrated in FIGS. 1-3.

In at least one embodiment, the delivery sleeve 20 has a generally conical shape which defines an entry opening 22 at one end of the delivery sleeve 20 and a relatively smaller exit opening 24 at an opposing, tapered terminal tip of the delivery sleeve 20. In at least one embodiment, as best illustrated in FIG. 1, the delivery sleeve 20 is constructed of a sufficiently flexible material, as discussed further below, which enables the delivery sleeve 20 to assume a flattened configuration for storage and shipping. In still further embodiments, any other material or combination of materials—now known or later developed—may be substituted, so long as the apparatus is capable of substantially carrying out the functionality described herein. Additionally, in at least one embodiment, the delivery sleeve 20 is constructed of a film material with a lubricious additive dispersed within the film during the processing of the film sheet. Slip is an additive that could be utilized in the film in at least one embodiment. Slip agents have a part that is soluble in the substrate and a part that is insoluble. During processing (in the molten phase), slip additives (as overall effect) are soluble and homogeneously dispersed in the substrate. Upon crystallization, the solubility limit is exceeded and the slip additive migrates from the matrix toward the surface, thus significantly reducing the coefficient of friction at the film surface. Anti-blocking additives may also be utilized in at least one embodiment. Anti-blocking helps prevent adjacent film layers from sticking to each other due to electrostatic charge or Van der Waals forces (attractive forces between polymer chains). Incorporating anti-blocking properties creates a micro-rough surface that reduces adhesion between adjacent film layers and helps prevent damage. Alternatively, in at least one embodiment, wax additives could be dispersed in the base material, such as polyurethane, to modify the surface appearance, feel, slip, abrasion resistance and overall durability of the film. The expense of additives integrated during the film manufacturing process is relatively low, especially compared to hydrophilic coatings applied to finished film. In at least one embodiment, the film could also be processed to have a textured surface to enhance lubricity. In still further embodiments, any other lubricant (or any other material or composition having sufficient lubricious properties), now known or later developed, may be substituted.

In at least one further embodiment, the funnel-shaped delivery sleeve 20, produced from film processed with additives for enhanced lubricity, could be augmented with an additional, separate surgical lubricant applied to an inner wall of the delivery sleeve 20. By way of a non-limiting example, common surgical lubricant such as Surgilube (H.R. Chemicals) is provided in a foil pack or tube. The lubricant could be water soluble in at least one embodiment, making residual lubricant that is transferred to the surgical breast pocket during prosthesis 10 insertion easy to be flushed and removed. In at least one embodiment, the surgical lubricant could be inexpensive, thereby resulting in a relatively more economically appealing apparatus.

In at least one further embodiment, the funnel-shaped delivery sleeve 20, produced from film processed with additives for enhanced lubricity, could be augmented with a hydrophilic coating. Due to the inherently lubricious nature of the film, the hydrophilic coating could require less demanding performance, and thus lower cost, thereby resulting in a relatively more economically appealing apparatus.

In at least one alternate embodiment, as illustrated best in FIGS. 4-8, the delivery sleeve 20 provides two opposingly joined, generally conical-shaped portions (hereinafter referred to as an entry portion 27 and an exit portion 23, respectively) which cooperate to define a entry opening 28 at one end of the delivery sleeve 20 (i.e., at a free end of the entry portion 27), an exit opening 24 at the opposing end of the delivery sleeve 20 (i.e., at a free end of the exit portion 23), and a relatively larger middle section 26 positioned therebetween (i.e., where the entry portion 27 is joined with the exit portion 23). As best illustrated in FIGS. 7 and 8, the entry portion 27 and exit portion 23 may be of differing shapes, sizes and/or materials. In at least one embodiment, the entry opening 28 and the exit opening 24 have a similar diameter. In at least one alternate embodiment, the entry opening 28 and exit opening 24 have different diameters. Additionally, in at least one embodiment, the entry portion 27 could be flexible and of relatively greater elasticity as compared to the exit portion 23, thus reducing the expansion pressure required for entry of the prosthesis 10 into the delivery sleeve 20. Similarly, in at least one embodiment, the exit segment 23 could be sufficiently flexible and of relatively lesser elasticity as compared to the entry portion 27, thus providing sufficient pressure to expel the prosthesis 10 from the delivery sleeve 20 with minimal expansion through the exit opening 24.

In at least one embodiment, as best illustrated in FIGS. 5 and 6, when a prosthesis 10, such as a silicone implant, is placed through the entry opening 28 into the interior of delivery sleeve 20, the delivery sleeve 20 is capable of being manipulated to conform to the shape of the prosthesis 10 as well as to apply pressure to direct the prosthesis 10 along a length of the delivery sleeve 20 and toward the exit opening 24.

In at least one embodiment, both the entry portion 27 and exit portion 23 are constructed of flexible materials. The materials could be compatible for joining the entry portion 27 and exit portion 23 by means of heat seal bonding, RF welding, adhesive bonding, or other appropriate means—now known or later developed. In at least one alternate embodiment, the entry portion 27 and exit portion 23 are of a single, unitary construction. In at least one embodiment, the exit portion 23 is constructed out of a fabric material such as a plastic-containing fabric, which is pliable yet resistant to stretching. In at least one further embodiment, the exit portion 23 may be constructed out of a transparent plastic or other suitable polymer material having sufficient properties including flexibility and low elasticity. It is believed that there are advantages to using a transparent or semitransparent material to assist the surgeon in proper orientation of the prosthesis 10 within the delivery sleeve 20. Suitable transparent materials may include vinyl, LDPE, polyurethane, and other similar materials—now known or later developed. As disclosed therein, suitable films heat sealed to form suitable containers, are transparent with minimal hazing, and can be sterilized using gas sterilization, irradiation sterilization, or heat with intact seals and remain sufficiently flexible and pliable for the necessary handling described herein.

In at least one embodiment, the entry portion 27 is flexible and elastic, could be made of a latex or other material with similar elastic properties—now known or later developed—to enable low pressure expansion of the entry opening 28 when inserting the prosthesis 10 through the entry opening 28. In at least one embodiment, the material of the entry portion 27 may be thin and have lattice structure to further enhance low pressure expansion.

Other attributes of the delivery sleeve 20, in at least one embodiment, include the ability for the delivery sleeve 20 to be a sterile component. Additionally, in at least one embodiment, an outer surface of the entry portion 27 and the interior surface of the exit portion 23 may have a low coefficient of friction to facilitate passage of the prosthesis 10 through the entry opening 28 and exit opening 24 respectfully. In at least one embodiment, the outer surface of the entry portion 27 and/or an outer surface of the exit portion 23 may be provided with a low coefficient of friction coating or lubricant. It has been found that using a surgically appropriate lubricant will facilitate passage of the prosthesis 10 through the interior of delivery sleeve 20. Such lubricants may be applied directly to the prosthesis 10 or the delivery sleeve 20 by the user, or the delivery sleeve 20 may be supplied pre-coated with a lubricant that is already present on the appropriate surfaces of the delivery sleeve 20.

In at least one embodiment, the entry portion 27 may have a tacky or high coefficient of friction inner surface 29 to improve the retention of the prosthesis 10 within the delivery sleeve 20. In this manner, the entry portion 27 acts as a one-way valve to releasably capture the prosthesis 10 within the delivery sleeve.

Since the size of the prosthesis 10 may vary in a range from about 150 cc to approximately 800 cc, the dimensions of each of the entry opening 28 and exit opening 24 may vary in order to accommodate various sizes for the prosthesis 10. In at least one embodiment, one or both of the exit opening 24 and entry opening 28 may be selectively enlarged by cutting portions of the delivery sleeve 20, proximal the corresponding end of the delivery sleeve 20, to provide for larger openings. In at least one embodiment, indicator the outer surface of the delivery sleeve 20 provides markings or other indicia positioned and configured for assisting with the cutting of the delivery sleeve 20 to the appropriate dimensions for the size of the prosthesis 10.

In at least one embodiment, the entry portion 27 is configured for being selectively inverted, as illustrated in FIG. 8. Accordingly, in such embodiments, when the prosthesis 10 is positioned within the entry portion 27, the entry opening 28 may expand in a similar manner as the exit opening 24 to enable the prosthesis 10 to traverse though the entry opening 28. After the implant is within the delivery sleeve 20, the entry opening 28 contracts back to a smaller size. Thereafter, the clinician is able to transport or manipulate the delivery sleeve 20 without the prosthesis 10 unintentionally escaping from the delivery sleeve 20. The clinician is thus able to apply pressure to the prosthesis 10, forcing the prosthesis 10 toward the exit opening 24. As illustrated in FIGS. 5 and 6, the prosthesis 10 can be forced through the exit opening 24.

Another aspect of the invention involves an exemplary method of placing the prosthesis 10 within the delivery sleeve 20, and placing the assembly within the appropriate sterile barrier packaging 30 (FIG. 9) prior to sterilization and shipment to the customer. In at least one embodiment, the sterile barrier packaging 30 could be a similar tray 32 and lid 34 commonly used for sterilization and shipment of implants. In at least one embodiment, the tray 32 could contain saline solution or other fluids to hydrate the prosthesis 10 and delivery sleeve 20. In at least one embodiment, the exemplary method would eliminate the concern of contamination in the operating room when the prosthesis 10 is being transferred and loaded into the delivery sleeve 20. In at least one embodiment, the entry opening 28 would aid in containing and maintaining the prosthesis 10 within the delivery sleeve 20 during transport. To further aid in containing and maintaining the prosthesis 10 within the delivery sleeve 20 during transport, one or both ends of the delivery sleeve 20 could be folded in a manner to obstruct the corresponding entry opening 28 and/or exit opening 24 so as to maintain the prosthesis 10 within the delivery sleeve 20. A manner of folding in at least one embodiment could be one or both ends folded down approximately 180 degrees and placed under the remainder of the delivery sleeve 20. Another manner of folding in at least one alternate embodiment could be one or both ends folded up 90 degrees, where a length of the tray 32 is such that the folded ends of the delivery sleeve 20 are in close proximity to opposing side walls of the tray 32.

Figure 10:
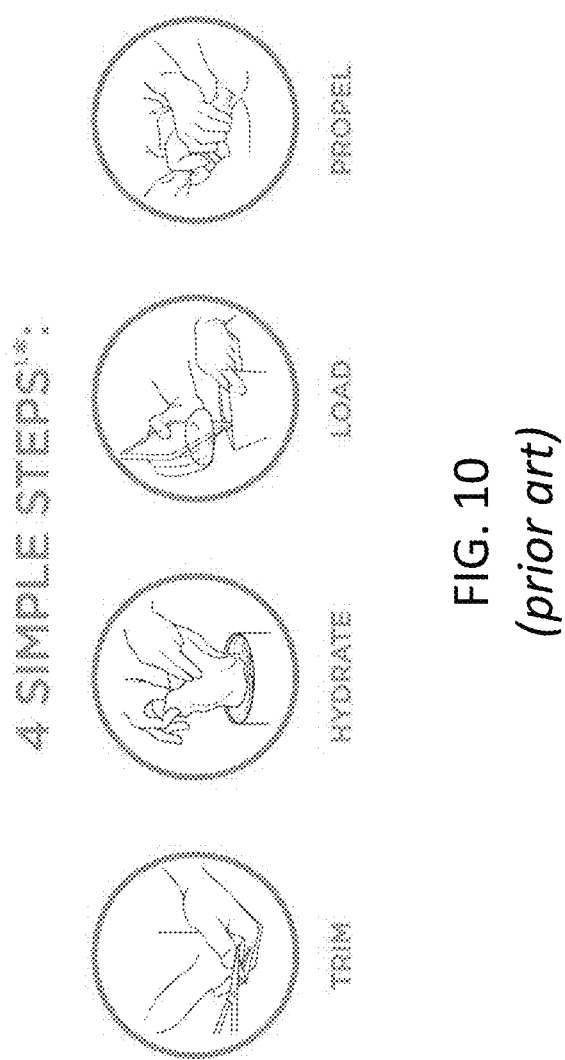
FIG. 10 is a diagram illustrating a prior art method for utilizing a prior art delivery sleeve to insert a silicone implant into a surgically developed pocket of a patient.

FIG. 10 provides a diagram that illustrates the known prior art funnel delivery method and handling of the prosthesis 10. Four steps are involved, three of which can expose the prosthesis 10 to contamination. By comparison, FIG. 11 provides a diagram that illustrates the exemplary method of utilizing the apparatus, where the prosthesis 10 is placed within the delivery sleeve 20 prior to being placed in the sterile barrier packaging 30.

The three steps which can expose the prosthesis 10 to contamination are eliminated, thus providing improved sterile integrity and cleanliness to the prosthesis 10.

Aspects of the present specification may also be described as the following embodiments:

1. A silicone prosthesis delivery apparatus for facilitating the transport and subsequent insertion of a silicone prosthesis into a surgically developed pocket of a patient, the apparatus comprising: a flexible, substantially funnel-shaped delivery sleeve for receiving and subsequently expelling the prosthesis therefrom, the delivery sleeve comprising: a substantially conical-shaped entry portion and a substantially conical-shaped exit portion, the entry portion and exit portion opposingly positioned and joined with one another so as to form a relatively larger diameter middle section; a tapered free end of the entry portion providing an entry opening configured for allowing the prosthesis to selectively pass therethrough when the prosthesis is inserted into the delivery sleeve; and a tapered free end of the exit portion providing an exit opening configured for allowing the prosthesis to selectively pass therethrough when the prosthesis is expelled from the delivery sleeve; whereby, with the prosthesis positioned within the delivery sleeve, the delivery sleeve is capable of being manipulated to conform to the shape of the prosthesis as well as to apply pressure to direct the prosthesis along a length of the delivery sleeve and toward the exit opening, such that the prosthesis may be expelled from the delivery sleeve through the exit opening.

2. The silicone prosthesis delivery apparatus according to embodiment 1, wherein the entry portion and exit portion have dimensions.

3. The silicone prosthesis delivery apparatus according to embodiments 1-2, wherein the entry portion and exit portion have different dimensions.

4. The silicone prosthesis delivery apparatus according to embodiments 1-3, wherein the entry portion has relatively smaller dimensions than the exit portion.

5. The silicone prosthesis delivery apparatus according to embodiments 1-4, wherein the delivery sleeve is constructed out of a flexible material.

6. The silicone prosthesis delivery apparatus according to embodiments 1-5, wherein the delivery sleeve is constructed out of a film material having a lubricious additive dispersed therewithin.

7. The silicone prosthesis delivery apparatus according to embodiments 1-6, wherein the lubricious additive is a slip agent.

8. The silicone prosthesis delivery apparatus according to embodiments 1-7, wherein the delivery sleeve provides a hydrophilic coating.

9. The silicone prosthesis delivery apparatus according to embodiments 1-8, wherein the film material is transparent or semi-transparent.

10. The silicone prosthesis delivery apparatus according to embodiments 1-9, wherein one or both of the entry portion and exit portion are constructed out of a flexible material having elastic properties.

11. The silicone prosthesis delivery apparatus according to embodiments 1-10, wherein the entry portion is relatively more elastic than the exit portion.

12. The silicone prosthesis delivery apparatus according to embodiments 1-11, wherein the delivery sleeve further provides an anti-blocking additive.

13. The silicone prosthesis delivery apparatus according to embodiments 1-12, wherein the delivery sleeve further provides a wax additive.

14. The silicone prosthesis delivery apparatus according to embodiments 1-13, wherein the delivery sleeve provides a textured surface for enhancing lubricity of the delivery sleeve.

15. The silicone prosthesis delivery apparatus according to embodiments 1-14, wherein an inner surface of the delivery sleeve provides a lubricant.

16. The silicone prosthesis delivery apparatus according to embodiments 1-15, wherein the entry portion is constructed out of a lattice structure for facilitating low pressure expansion of the entry portion when the prosthesis is inserted through the entry opening.

17. The silicone prosthesis delivery apparatus according to embodiments 1-16, wherein an inner surface of the entry portion has a sufficient coefficient of friction for preventing the prosthesis from exiting the delivery sleeve through the entry opening.

18. The silicone prosthesis delivery apparatus according to embodiments 1-17, wherein the delivery sleeve is capable of being cut proximal one or both of the entry opening and exit opening, thereby allowing one or both of the entry opening and exit opening to be selectively enlarged to better accommodate the prosthesis as needed.

19. The silicone prosthesis delivery apparatus according to embodiments 1-18, wherein an outer surface of the delivery sleeve provides markings or other indicia positioned and configured for assisting with the cutting of the delivery sleeve.

20. The silicone prosthesis delivery apparatus according to embodiments 1-19, wherein the entry portion is capable of being selectively inverted when the prosthesis is inserted through the entry opening.

21. The silicone prosthesis delivery apparatus according to embodiments 1-20, further comprising a sterile barrier packaging configured for storing and maintaining the sterilization of the delivery sleeve and prosthesis prior to use.

22. The silicone prosthesis delivery apparatus according to embodiments 1-21, wherein a tray of the barrier packaging contains a volume of an at least one fluid for hydrating the delivery sleeve and prosthesis.

23. A silicone prosthesis delivery apparatus comprising: a silicone prosthesis; and a flexible, substantially funnel-shaped delivery sleeve configured for receiving and subsequently expelling the prosthesis therefrom, the delivery sleeve comprising: a substantially conical-shaped entry portion and a substantially conical-shaped exit portion, the entry portion and exit portion opposingly positioned and joined with one another so as to form a relatively larger diameter middle section; a tapered free end of the entry portion providing an entry opening configured for allowing the prosthesis to selectively pass therethrough when the prosthesis is inserted into the delivery sleeve; a tapered free end of the exit portion providing an exit opening configured for allowing the prosthesis to selectively pass therethrough when the prosthesis is expelled from the delivery sleeve; whereby, with the prosthesis positioned within the delivery sleeve, the delivery sleeve is capable of being manipulated to conform to the shape of the prosthesis as well as to apply pressure to direct the prosthesis along a length of the delivery sleeve and toward the exit opening, such that the prosthesis may be expelled from the delivery sleeve through the exit opening.

24. A method for preparing the silicone prosthesis delivery apparatus of claim 1, the method comprising the steps of: inserting a prosthesis through the entry opening of the entry portion of the delivery sleeve, such that the prosthesis is positioned within the delivery sleeve; folding each of the opposing ends of the delivery sleeve so as to obstruct each of the entry opening and exit opening, thereby preventing the prosthesis from unintentionally exiting the delivery sleeve; and positioning the delivery sleeve within a sterile barrier packaging.

25. The method according to embodiment 24, further comprising the step of folding each of the opposing ends of the delivery sleeve so as to obstruct each of the entry opening and exit opening, thereby preventing the prosthesis from unintentionally exiting the delivery sleeve.

26. The method according to embodiments 24-25, further comprising the step of placing a volume of an at least one fluid into a tray of the barrier packaging for hydrating the delivery sleeve and prosthesis.

27. The method according to embodiments 24-26, wherein the step of folding each of the opposing ends of the delivery sleeve further comprises the step of folding each of the opposing ends down approximately 180 degrees and placing the folded ends under the remainder of the delivery sleeve.

28. The method according to embodiments 24-27, wherein the step of folding each of the opposing ends of the delivery sleeve further comprises the step of folding each of the opposing ends up approximately 90 degrees such that the folded ends are in close proximity to opposing side walls of a tray of the barrier packaging.

In closing, regarding the exemplary embodiments of the present invention as shown and described herein, it will be appreciated that a silicone prosthesis delivery apparatus and configured for facilitating the transport and subsequent insertion of a silicone prosthesis into a surgically developed pocket of a patient is disclosed. Because the principles of the invention may be practiced in a number of configurations beyond those shown and described, it is to be understood that the invention is not in any way limited by the exemplary embodiments, but is generally directed to a silicone prosthesis delivery apparatus and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the methods and the order in which the respective elements of each method are performed are purely exemplary. Depending on the implementation, they may be performed in any order or in parallel, unless indicated otherwise in the present disclosure.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A silicone prosthesis delivery apparatus for facilitating the transport and subsequent insertion of a silicone prosthesis into a surgically developed pocket of a patient, the apparatus comprising:
    a flexible, substantially funnel-shaped delivery sleeve configured for receiving and subsequently expelling the prosthesis therefrom, the delivery sleeve comprising:
        a substantially conical-shaped entry portion and a substantially conical-shaped exit portion, the entry portion and exit portion opposingly positioned and joined with one another so as to form a relatively larger diameter middle section, the entry portion further configured for being temporarily inverted so as to be positioned within the exit portion during insertion of the prosthesis therein;
        a tapered free end of the entry portion providing a stretchable entry opening configured for allowing the prosthesis to traverse along an outer surface of the entry portion, when the entry portion is inverted and positioned within the exit portion, and pass through the entry opening to a position inside the exit portion; and
        a tapered free end of the exit portion providing a stretchable exit opening configured for allowing the prosthesis to pass therethrough when the prosthesis is expelled from the exit portion;
        the diameter of the middle section being relatively larger than a diameter of each of the entry opening and exit opening;
    whereby, with the prosthesis positioned within the exit portion of the delivery sleeve, the delivery sleeve is capable of being manipulated to apply pressure to direct the prosthesis along a length of the exit portion of the delivery sleeve and toward the exit opening, such that the prosthesis may be expelled from the delivery sleeve through the exit opening.

2. The silicone prosthesis delivery apparatus of claim 1, wherein the entry opening has a diameter that is equal to or less than a diameter of the exit opening.

3. The silicone prosthesis delivery apparatus of claim 1, wherein the delivery sleeve is constructed out of a flexible material.

4. The silicone prosthesis delivery apparatus of claim 3, wherein the delivery sleeve is constructed out of a film material having a lubricious additive dispersed therewithin.

5. The silicone prosthesis delivery apparatus of claim 4, wherein the lubricious additive is a slip agent.

6. The silicone prosthesis delivery apparatus of claim 4, wherein the delivery sleeve provides a hydrophilic coating.

7. The silicone prosthesis delivery apparatus of claim 3, wherein one or both of the entry portion and exit portion are constructed out of a flexible material having elastic properties.

8. The silicone prosthesis delivery apparatus of claim 7, wherein the entry portion is relatively more elastic than the exit portion.

9. The silicone prosthesis delivery apparatus of claim 1, wherein the delivery sleeve provides a textured surface for enhancing lubricity of the delivery sleeve.

10. The silicone prosthesis delivery apparatus of claim 1, wherein an inner surface of the delivery sleeve provides a lubricant.

11. The silicone prosthesis delivery apparatus of claim 1, wherein the entry portion is constructed out of a lattice structure for facilitating low pressure expansion of the entry portion when the prosthesis is inserted through the entry opening.

12. The silicone prosthesis delivery apparatus of claim 1, wherein an inner surface of the entry portion has a sufficient coefficient of friction for preventing the prosthesis from exiting the delivery sleeve through the entry opening.

13. The silicone prosthesis delivery apparatus of claim 1, further comprising a sterile barrier packaging configured for storing and maintaining the sterilization of the delivery sleeve and prosthesis prior to use.

14. The silicone prosthesis delivery apparatus of claim 13, wherein a tray of the barrier packaging contains a volume of an at least one fluid for hydrating the delivery sleeve and prosthesis.

15. A silicone prosthesis delivery apparatus comprising:
    a silicone prosthesis; and
    a flexible, substantially funnel-shaped delivery sleeve configured for receiving and subsequently expelling the prosthesis therefrom, the delivery sleeve comprising:
        a substantially conical-shaped entry portion and a substantially conical-shaped exit portion, the entry portion and exit portion opposingly positioned and joined with one another so as to form a relatively larger diameter middle section, the entry portion further configured for being temporarily inverted so as to be positioned within the exit portion during insertion of the prosthesis therein;
        a tapered free end of the entry portion providing a stretchable entry opening configured for allowing the prosthesis to traverse along an outer surface of the entry portion, when the entry portion is inverted and positioned within the exit portion, and pass through the entry opening to a position inside the exit portion; and
        a tapered free end of the exit portion providing a stretchable exit opening configured for allowing the prosthesis to pass therethrough when the prosthesis is expelled from the exit portion;
    whereby, with the prosthesis positioned within the exit portion of the delivery sleeve, the delivery sleeve is capable of being manipulated to apply pressure to direct the prosthesis along a length of the exit portion of the delivery sleeve and toward the exit opening, such that the prosthesis may be expelled from the delivery sleeve through the exit opening.

\* \* \* \* \*